(12) United States Patent
Matusewicz et al.

(10) Patent No.: US 7,488,450 B2
(45) Date of Patent: Feb. 10, 2009

(54) ANALYTE COLLECTION AND DETECTION DEVICES

(75) Inventors: Richard S. Matusewicz, San Jose, CA (US); Martha L. Hay-Kaufman, Los Altos, CA (US); John Doherty, Palm Desert, CA (US); Leslie Goulden, Los Altos, CA (US); Geeta S. Kalbag, Milpitas, CA (US); Corey L. Jaseph, Boulder Creek, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 731 days.

(21) Appl. No.: 10/794,370

(22) Filed: Mar. 4, 2004

(65) Prior Publication Data

US 2005/0196318 A1 Sep. 8, 2005

(51) Int. Cl.
*G01N 31/32* (2006.01)

(52) U.S. Cl. .............................. 422/58; 422/50; 422/61; 422/68.1; 422/100

(58) Field of Classification Search ............. 422/55–58, 422/68.1, 82.05–82.11; 436/164–172
See application file for complete search history.

(56) References Cited

U.S. PATENT DOCUMENTS

| | | | | |
|---|---|---|---|---|
| 3,996,006 A | 12/1976 | Pagano | ......................... | 422/50 |
| 4,225,557 A | 9/1980 | Hartl et al. | ..................... | 422/56 |
| 4,486,536 A * | 12/1984 | Baker et al. | ................... | 436/66 |
| 4,645,743 A * | 2/1987 | Baker et al. | ................... | 436/66 |
| 4,789,629 A | 12/1988 | Baker et al. | ..................... | 435/7 |
| 5,064,766 A | 11/1991 | Wardlaw et al. | .............. | 436/66 |
| 5,100,619 A | 3/1992 | Baker et al. | ................... | 422/58 |
| 5,106,582 A | 4/1992 | Baker | .......................... | 422/58 |
| 5,171,529 A | 12/1992 | Schreiber | ..................... | 422/58 |
| 5,182,191 A | 1/1993 | Fan et al. | ..................... | 435/7.9 |
| 5,264,181 A * | 11/1993 | Schreiber | ..................... | 422/58 |
| 5,441,698 A | 8/1995 | Norell | .......................... | 422/58 |
| 5,747,344 A * | 5/1998 | Cleator | ........................ | 436/66 |
| 5,747,351 A | 5/1998 | Hemmati | ..................... | 436/514 |
| 5,846,838 A | 12/1998 | Chandler | ..................... | 436/514 |
| 5,877,028 A | 3/1999 | Chandler et al. | ............ | 436/514 |
| 5,879,951 A * | 3/1999 | Sy | .............................. | 436/514 |
| 5,939,252 A * | 8/1999 | Lennon et al. | .................. | 435/4 |
| 5,998,220 A | 12/1999 | Chandler | ..................... | 436/514 |
| 6,017,767 A | 1/2000 | Chandler | ..................... | 436/514 |
| 6,033,627 A | 3/2000 | Shields et al. | .................. | 436/58 |

(Continued)

FOREIGN PATENT DOCUMENTS

EP 0 239 265 3/1987

(Continued)

*Primary Examiner*—Alexa D Neckel
*Assistant Examiner*—Imran Akram
(74) *Attorney, Agent, or Firm*—Morrison & Foerster LLP

(57) ABSTRACT

A system for collecting biological samples, such as fecal specimens, and testing such samples for the presence of an analyte is disclosed. The system comprises a sample collection device that includes a removably secured tab for retaining and transferring a portion of the sample to be tested to the test device. The tab is preferably configured so that it can be received in the test device in only a pre-selected orientation so as to put the portion of the tab carrying the sample in communication with a chromatographic material in the test device.

17 Claims, 7 Drawing Sheets

U.S. PATENT DOCUMENTS

| | | | |
|---|---|---|---|
| 6,087,184 A * | 7/2000 | Magginetti et al. | 436/514 |
| 6,165,416 A | 12/2000 | Chandler | 422/58 |
| 6,168,956 B1 | 1/2001 | Chandler | 436/514 |
| 6,221,678 B1 | 4/2001 | Chandler | 436/530 |
| 6,271,046 B1 | 8/2001 | Chandler | 436/530 |
| 6,436,714 B1 * | 8/2002 | Clawson et al. | 436/66 |
| 6,528,321 B1 * | 3/2003 | Fitzgerald et al. | 436/514 |

FOREIGN PATENT DOCUMENTS

| | | |
|---|---|---|
| WO | WO 00/54024 | 9/2000 |
| WO | WO 2004/033101 | 4/2004 |

* cited by examiner

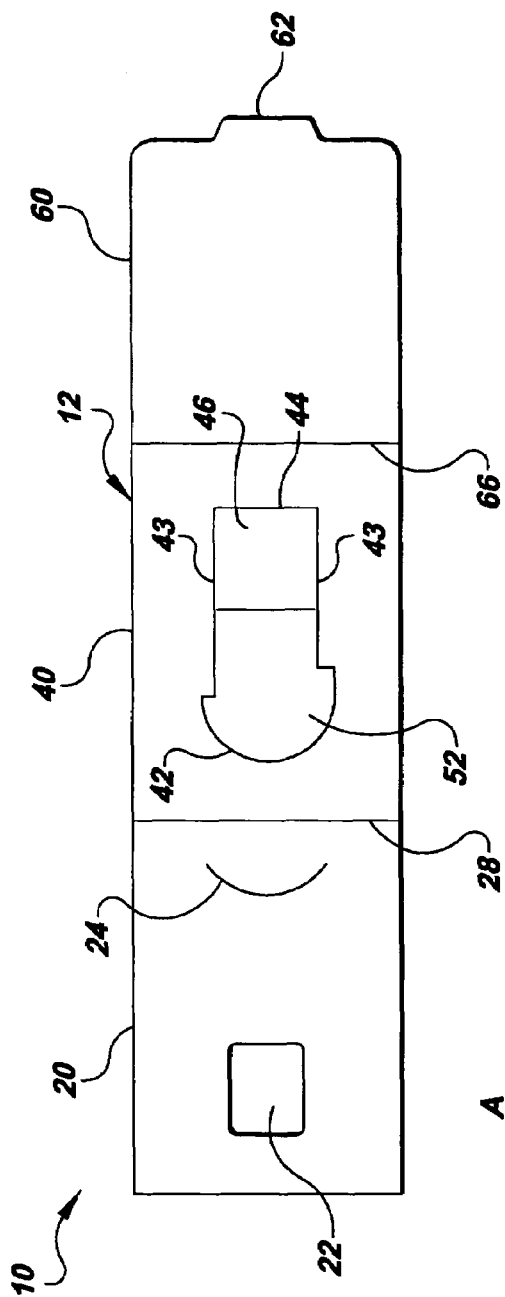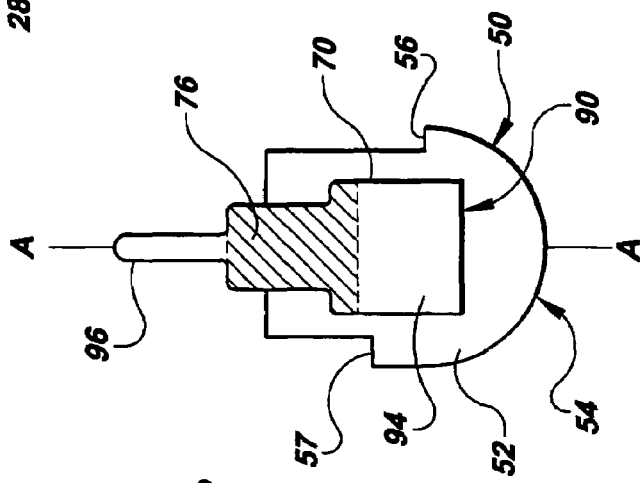

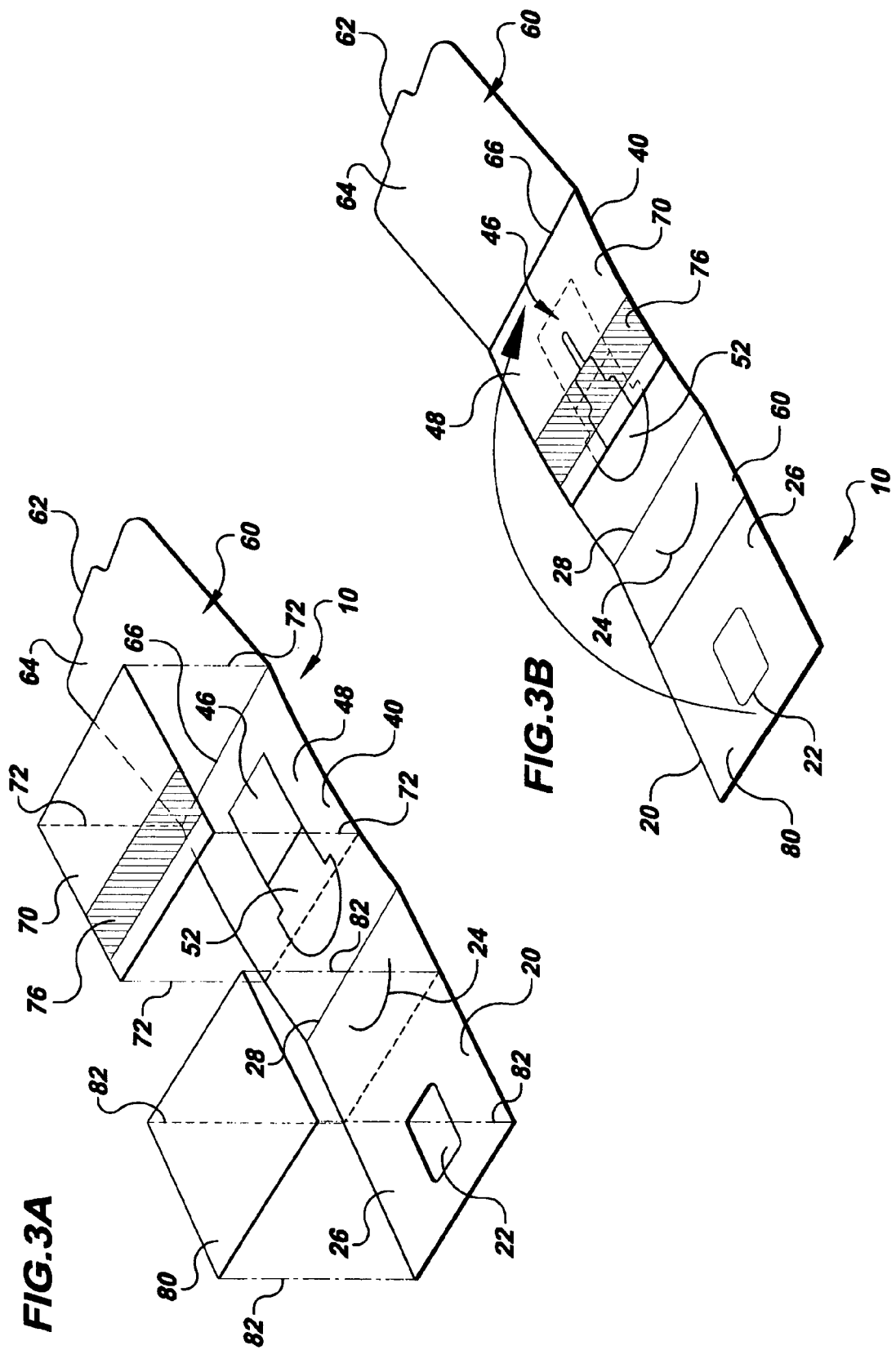

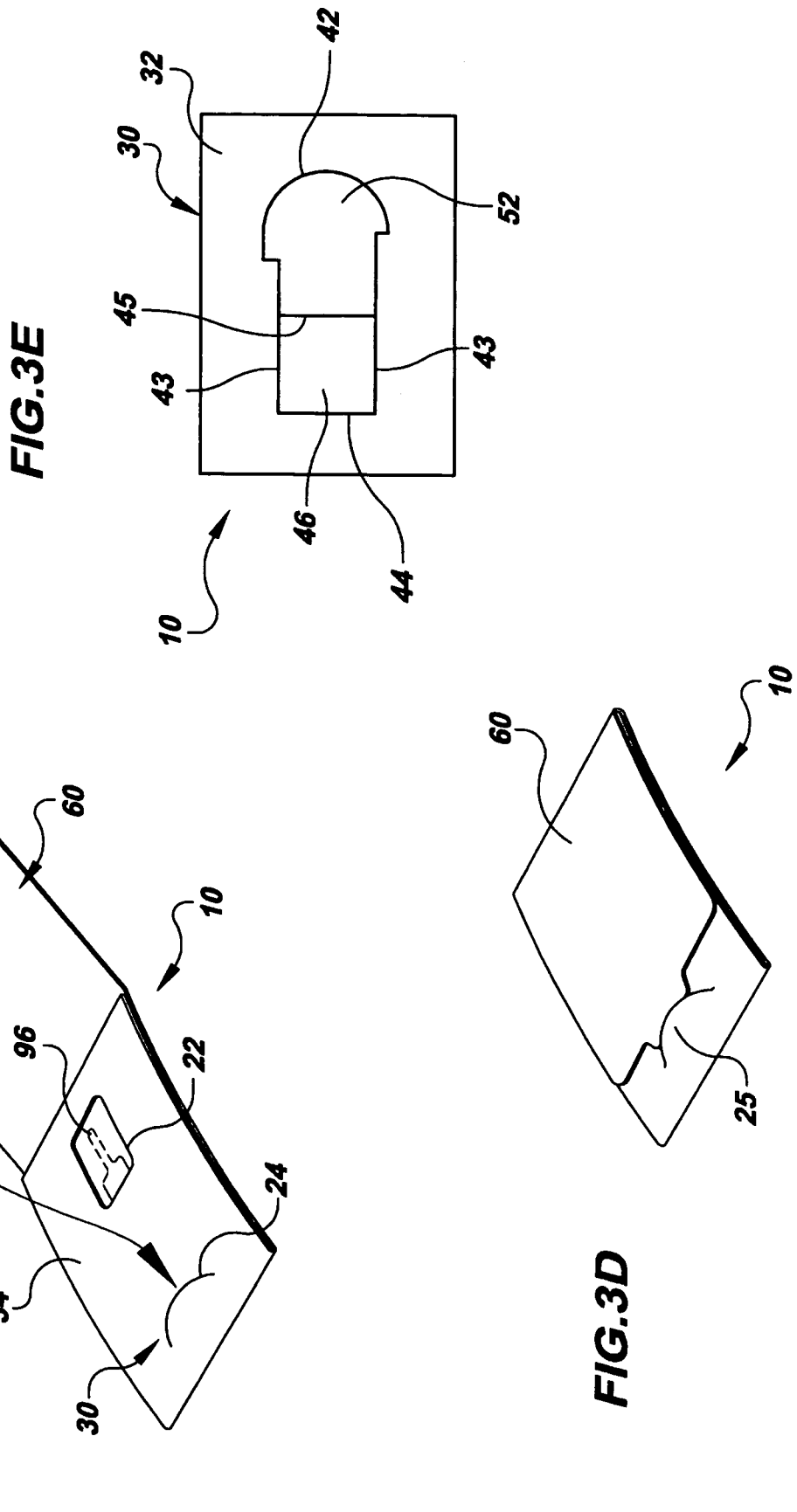

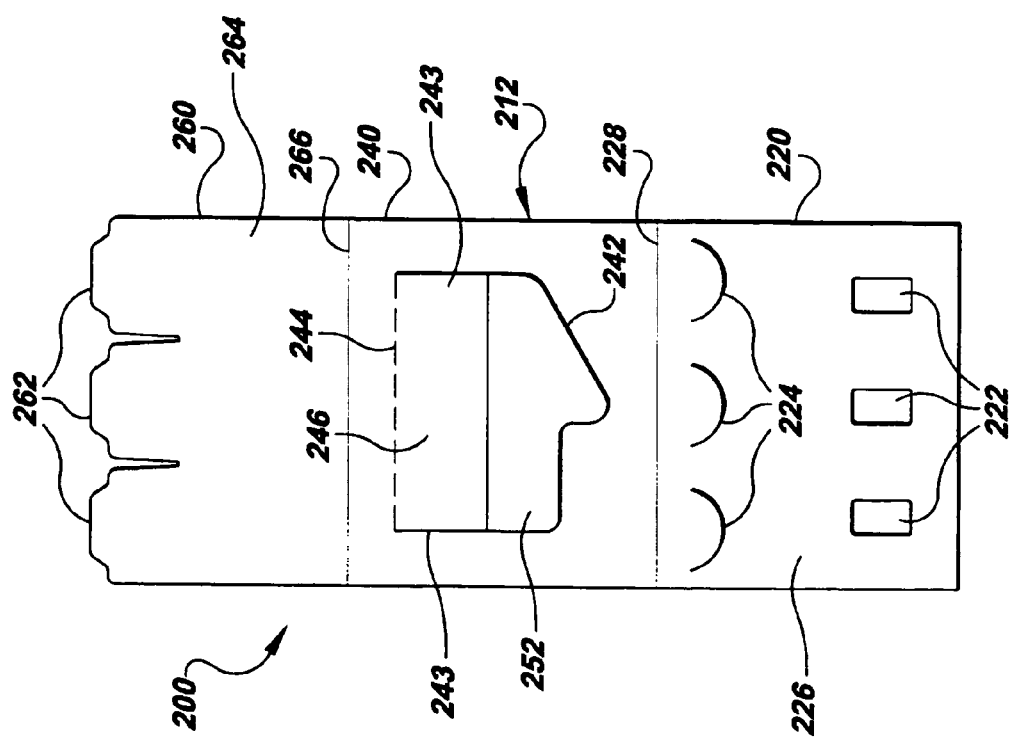
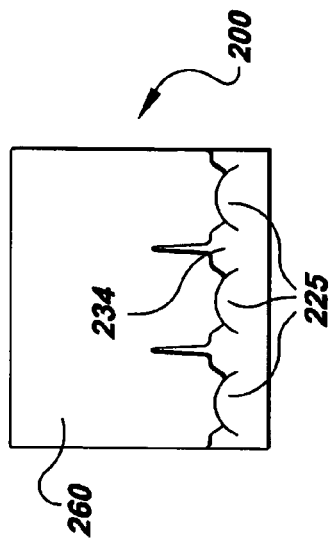
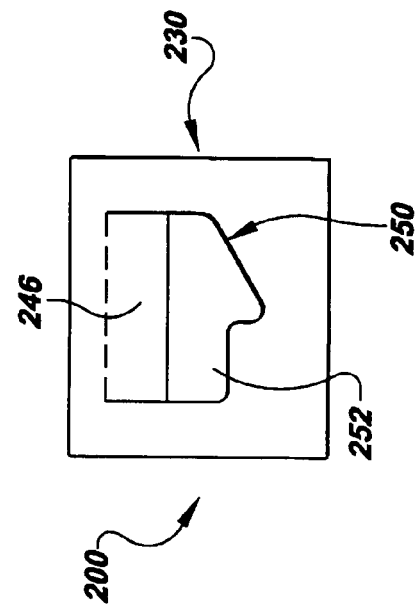

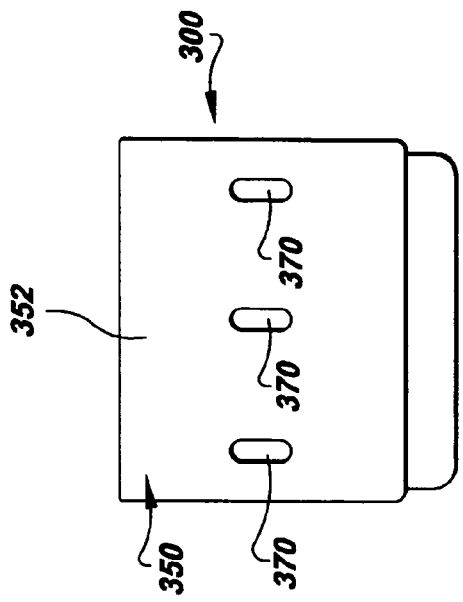
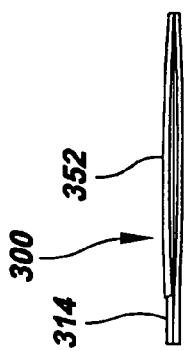
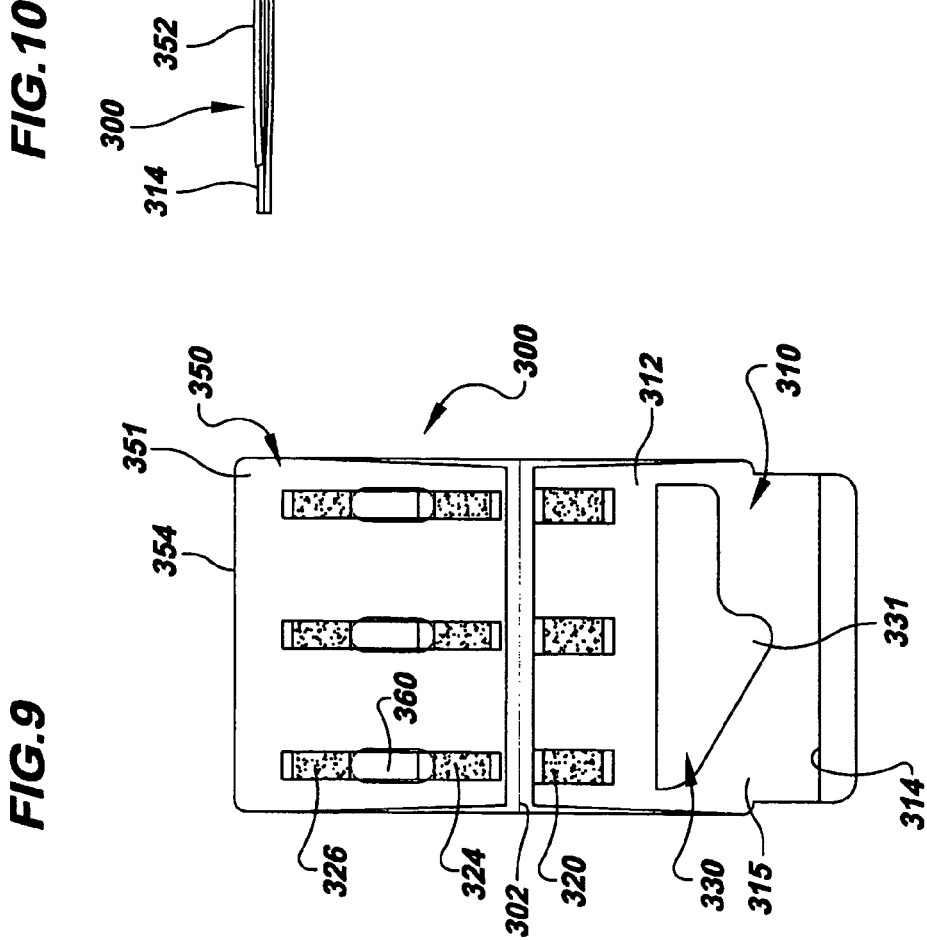

ANALYTE COLLECTION AND DETECTION DEVICES

BACKGROUND OF THE INVENTION

The present invention is directed to a system for collecting a sample possibly containing an analyte of interest and for then testing the sample. The invention is particularly directed to an improved system for detecting an analyte of interest in a fecal sample. Testing for blood in fecal samples, referred to as a fecal occult blood (FOB) test, for example is commonly performed as a screen for colorectal cancer.

A variety of FOB formats are known in the art (see e.g., U.S. Pat. Nos. 3,996,006; 4,225,557; 4,789,629; 5,064,766; 5,100,619; 5,106,582; 5,171,529; and 5,182,191). The majority of such test formats are based on the chemical detection of heme groups present in stool as a breakdown product of blood. In such tests, the pseudoperoxidase nature of the heme group is used to catalyze a colorimetric reaction between an indicator dye and peroxide. The oxygen sensitive dye can be gum guaiac, orthodianisidine, tetramethylbenzidine, or the like, with guaiac being preferred.

Analytes, including analytes present in stool, can also be detected using chromatographic assay systems. Chromatographic assays, and in particular immunochromatographic assays, are frequently used by physicians and medical technicians for rapid in-office diagnosis and therapeutic monitoring of a variety of conditions and disorders. Immunoassays depend on the specific interaction between an antigen or hapten and a corresponding antibody. In immunochromatographic assays, a detecting reagent or particle is linked to an antibody which binds specifically to a molecule to be assayed, forming a conjugate. This conjugate is then mixed with a specimen and, if the molecule to be assayed is present in the specimen, the detecting reagent-linked antibodies bind to the molecule, thereby giving an indication that the molecule is present. The detecting reagent or particle can be identifiable by color, magnetic properties, specific reactivity with another molecule, or another physical or chemical property.

More information regarding such analytical test systems can be found for example in U.S. Pat. Nos. 4,789,629; 5,441, 698; 5,877,028; 6,017,767; 6,165,416; 6,168,956; 6,033,627; 5,846,838; 5,747,351 and 6,221,678, all of which are incorporated herein by reference. In order to make use of such systems, of course, a sample to be tested must first be obtained. In the case of samples obtained from a location away from a physician's office or laboratory able to perform an assay, the sample must be appropriately collected and then transported to the test site.

The collection of fecal samples for testing presents particular challenges, both to the individuals providing such samples as well as to the technicians testing them. Samples obtained away from a testing laboratory must be mailed or otherwise transported, and when received at a laboratory need to be handled without exposing technicians to such samples. The collected samples further need to be appropriately tested. There remains a need for better methods and devices for collecting such samples, transferring the samples to test devices, and performing assays, in particular to facilitate the transfer of a sample to a test device while minimizing the possibility of exposure of a technician to the sample.

SUMMARY OF THE INVENTION

The present invention provides improved devices and methods for collecting, transferring, and testing a sample, in particular a fecal sample for use in diagnosis of a medical condition. One aspect of the invention comprises a sample test device having a test device body, a receptacle in the body adapted to receive a sample carrying member, and a cover member adapted to be placed onto the body. The sample carrying member is bilaterally asymmetrical, and the receptacle is sized and shaped so that the sample carrying member can be received in only a pre-selected orientation. The cover includes a piece of chromatographic material, and the cover member and receptacle cooperate so as to place the chromatographic material in communication with a sample when the sample carrying member is contained in the receptacle in the pre-selected orientation, and when the cover is attached to the body. Preferably, the cover member is attached to the body with a hinge, or alternatively can be adapted to be reversibly attached to the body. The body can be made from an upper and lower layer of material, in which case the receptacle comprises an opening in the upper layer of material. The cover member can further include a window, and the chromatographic material then preferably extends across the window. An immobilized capture reagent which binds an analyte of interest is present in the portion of the chromatographic material located in the window in such an embodiment.

In another aspect, the chromatographic material of the test device is attached to the body of the test device instead of to the cover. The cover in this embodiment is optional, but if used is preferably adapted to be attached to the body, such as with a hinge.

A further aspect of the present invention comprises a sample collection device comprising a body having a substantially planar surface; a sample tab with a handle removably secured to the substantially planar surface, an absorbent material for receiving a sample attached to the sample tab and extending beyond the distal end of the handle, and a flap attached to the substantially planar surface. The flap has a proximal edge covering at least a portion of the absorbent material of the sample tab when the sample tab is removably secured to the first opposed surface. The proximal edge of the flap is adapted to extend away from the substantially planar surface so as to provide clearance for the absorbent material when the sample tab is removed from the surface. The handle and flap are preferably integrally formed from the substantially planar surface of the collection device. In one embodiment, the absorbent material is impregnated with a band of moisture barrier material separating a sample collection end of the absorbent material from the remainder of the absorbent material. The body of the device also preferably includes a window in a surface opposite the substantially planar surface which is in communication with the absorbent material. The window can further include a filter material which allows liquid to flow through the filter material but which inhibits the flow of solids. A cover over the window is also preferably included.

Another aspect of the present invention comprises a system for collecting and testing a sample that includes a sample collection device and a test device. The sample collection device includes a sample tab for receiving a sample which is removably secured to the sample collection device and has a configuration which is bilaterally asymmetrical. The test device includes a body, a receptacle in the body adapted to receive the sample tab from the sample collection device, and a cover member adapted to be attached to the body which includes a piece of chromatographic material. The receptacle is sized and shaped so that the sample tab can be received in only a pre-selected orientation. The sample tab, cover member and receptacle cooperate so as to place the chromatographic material in communication with the sample tab when the sample tab is contained in the receptacle in the pre-selected orientation and when the cover member is attached to the test device body.

The sample tab preferably comprises an absorbent material which is impregnated with a band of moisture barrier material separating a sample collection end of the absorbent material from the remainder of the absorbent material in the sample tab. The cover member of the test device also preferably further includes a window having chromatographic material extending across it, and an immobilized capture reagent which binds an analyte of interest is then preferably present in the portion of the chromatographic material located in the window. The body of the test device can further include a sample pad and a cushioning material between the sample pad and the body.

In yet another aspect, the present invention comprises a method of testing for an analyte in a sample. In this method a sample carrying member which is bilaterally asymmetrical and which carries a sample is received by an individual responsible for carrying out the test or assay, and it is placed in a receptacle of a test device in a pre-selected orientation. The receptacle is sized and shaped so that the sample carrying member can be received in the receptacle only in the pre-selected orientation. A test to determine whether the sample contains the analyte is then performed. The test can include adding an assay buffer to the sample carrying member and then placing a cover on the test device, in which case the cover comprises a chromatographic material with a detection reagent, and placing the cover on the test device places the chromatographic material in communication with the sample in the sample carrying member. The test can further include observing a visible indicator of the assay result on the chromatographic material through a window in the cover. In a preferred embodiment, the sample carrying member is removed from a sample collection device to which it is removably secured prior to testing.

BRIEF DESCRIPTION OF THE FIGURES

These and other features, aspects, and advantages of the present invention will become better understood with reference to the following description, appended claims, and accompanying drawings where:

FIG. 1 is a top plan view of a blank from which a sample collection device of the present invention can be made.

FIG. 2 is a top plan view of a sample collection tab according to the present invention.

FIG. 3A is a perspective view of the blank of FIG. 1 with the placement of two additional sheets of material on this blank.

FIG. 3B is a perspective view showing the folding of the completed blank of FIG. 3A along fold line 28.

FIG. 3C is a perspective view showing the folding of the blank of FIG. 3B along fold line 66.

FIG. 3D is a perspective view of the assembled sample collection device.

FIG. 3E is a bottom plan view of the exterior side of the base member of the collection device.

FIG. 6 is a top plan view of a blank from which an alternative embodiment of the collection device of the present invention can be made.

FIG. 7 is a top plan view of the exterior side of the cover member of the assembled sample collection device of FIG. 6.

FIG. 8 is a bottom plan view of the exterior side of the base member of the assembled sample collection device of FIG. 6.

FIG. 9 is a top plan view of an alternative embodiment of the test device of the present invention designed for use with the sample collection device of FIGS. 6-8.

FIG. 10 is a side elevation view of the test device of FIG. 9 in a closed position.

FIG. 11 is a top plan view of the test device of FIG. 9 in a closed position.

DETAILED DESCRIPTION OF THE INVENTION

Figure 5A:
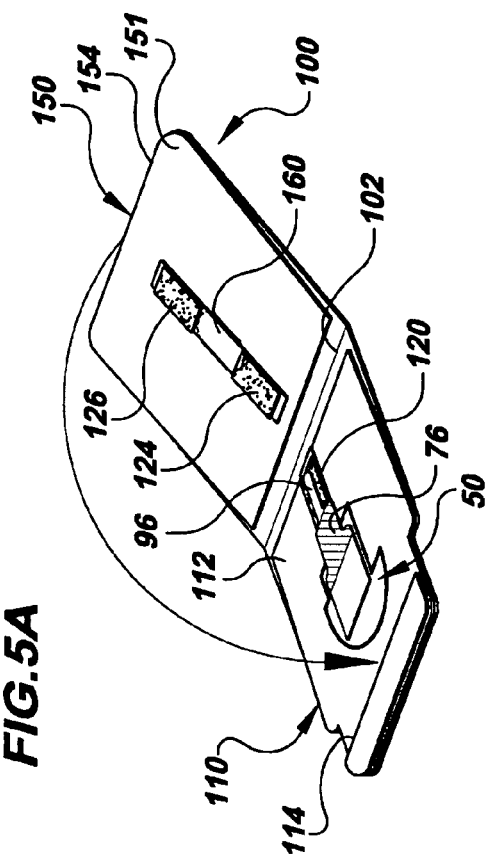
FIG. 5A is a perspective view of the interior side of the test device shown in FIG. 4 with the sample collection tab placed in the test device, and depicting the closure of the test device in order to perform a test according to the present invention.

FIGS. 1-3E illustrate the construction of a preferred embodiment of a sample collection device 10 having features of the present invention. A blank 12 is preferably die-cut or otherwise formed from a piece of rigid material as shown in FIG. 1. The rigid material is preferably a cellulose-based material that is resistant to moisture such as cardboard, paperboard and fiberboard, the surfaces of which have been treated so as to make them moisture resistant, such as through the application of a varnish or laminate material. A preferred material is solid bleached sulfite (SBS) paperboard approximately 0.024 inches thick. Alternatively, the rigid material can be a plastic that is resistant or impervious to moisture such as polypropylene, polyethylene, polystyrene, acrylic, or polycarbonate plastic.

The blank 12 includes a cover member portion 60, a center portion 40 and a window portion 20. The center portion 40 and the window portion 20 cooperate to form a base member 30, as described below. The center portion 40 includes a sample tab perforation 42 around the entire periphery of sample tab backing 52. Sample tab perforation 42 is not a complete perforation, i.e. it can comprise a line of cuts or holes, or it can comprise a partial cut into the rigid material of the blank 12 (i.e. the cut does not extend entirely through the rigid material), such that sample tab backing 52 remains connected to the remainder of the blank 12 until separated from the sample collection device 10 through the application of pressure or other force to the sample tab backing 52 by a user. It is preferred that the handle end 54 of the sample tab 50 however comprise a complete perforation. Perforations in detachment flap sides 43 can be complete cuts through the rigid material, or like the sample tab perforation can comprise incomplete or partial perforations of the rigid material. Such perforations cooperate with distal flap edge 44 as well as with a portion of the sample tab perforation 42 to form the detachment flap 46.

The window portion 20 includes an opening or window 22 cut from the blank 12. The window portion 20 further includes a tab lock perforation 24 used to form tab lock 25 (shown in FIG. 3D). The tab lock 25 cooperates with a tab 62 on the cover member 60 when the sample collection device 10 is assembled to maintain the sample collection device 10 in a closed position. Tab lock perforation 24 can be a complete perforation or, like the perforations in detachment flap sides 43, can comprise either incomplete or partial perforations of the rigid material.

As best shown in FIGS. 3A-3E, a sample collection device 10 can be constructed from the blank 12 through the addition of absorbent material 70 and filter material 80. The absorbent material 70 and filter material 80 are placed on and adhered to the collection device 10 as shown in FIG. 3A. Absorbent material 70 is placed on the center portion 40 along placement lines 72 so as to cover the detachment flap 46 and at least a portion of sample tab backing 52. The filter material 80 is placed on the window portion 20 of the blank 12 so as to cover the window 22. For ease of manufacturing the absorbent material 70 and filter material 80 can cover the entire width of the blank 12 as shown in the embodiment shown in FIGS. 3A and 3B and can be cut from continuous bands of such materials, but the absorbent material 70 and filter material 80 can also cover less area.

The absorbent material 70 is a material which is more absorbent than the material from which the sample tab backing 52 is made and which is able to hold and/or reversibly bind an analyte of interest, but which doesn't react with or permanently bind the analyte under test conditions. The absorbent material 70 can comprise, for example, an open-cell, chemically inert matrix, such as porous plastic, filter paper, glass fiber, or a combination of filter paper and glass fiber, which doesn't bind or react with an analyte of interest. In one embodiment, the absorbent material 70 can comprise a cotton cellulose fiber-based filter paper such as Type 950, manufactured by Ahlstrom Filtration, Inc (Helsinki, Finland). Such materials allow rapid and complete desiccation of a liquid sample carrying an analyte of interest, and minimize the possibility of sample breakdown due, for example, to continued exposure to a liquid environment. The absorbent material can also be pre-impregnated with materials for removing or disguising any odors from, e.g., a fecal specimen.

The filter material 80 is selected to separate any solid portions of a sample from a liquid portion, such that the liquid passes through the filter together with an analyte of interest but the solid portion does not. In one embodiment of the present invention, used to collect biological samples, the porosity of the filter is selected to filter out cellular or particulate matter in samples such as whole blood or fecal specimens. The filter material 80 thus acts as a screen to allow liquid to flow through the window 22 but to inhibit the flow of sample solids through the window 22 and subsequently into the absorbent material 70 of the sample tab 50. The filter material 80 also preferably should not bind or react with an analyte of interest for which an assay is to be performed with the test device 100.

Suitable materials that can be used for the filter material 80 include porous plastic, cellulose, paper, nylon, rayon, glass fiber, polyester mesh, and non-woven synthetic fabrics which preferably have tensile strength, are resistant to tearing, and do not bind or react with an analyte of interest. One such material is the type of fine mesh material used for tea bags, such as type HO3249 nonwoven polyester teabag paper manufactured by Ahlstrom Filtration, Inc.

In one embodiment (not illustrated), the absorbent material 70 and filter material 80 are bonded together or otherwise brought into physical contact prior to being attached to the sample collection device 10, rather than being applied separately to the sample collection device 10. In this embodiment the absorbent material face of the combined absorbent material 70 and filter material 80 can be adhered first to the center portion 40, after which the window portion 20 would be bent along fold line 28 to bring the interior side 26 of the window portion 20 into contact with the filter paper 80. Alternatively the filter paper face of the combined absorbent material 70 and filter material 80 can be adhered first to the interior surface 26 of the window portion 20, after which the window portion 20 would be bent along fold line 28 to bring the absorbent material 80 into contact with the center portion 40.

The adhesive is preferably used to adhere the absorbent material and filter material preferably is one that isn't soluble in the sample liquid containing an analyte of interest, and for the absorbent material 70 the adhesive shouldn't be soluble in the reagents applied to the sample collection end 96 in the detection of the analyte. One adhesive that can be used is a composition comprising vinyl acetate and starch such as National Starch adhesive #38-4536. The adhesive can be applied in drops or dollops onto the center portion 40 and the window portion 20 prior to contacting the absorbent material 70 and filter material 80. Alternatively a band of adhesive material may be applied to center portion 40 and/or the window portion 20, or the adhesive may instead or in addition be applied to the absorbent material 70 and/or the filter material 80 prior to contacting the sample collection device 10. With regard to the absorbent material 70 on the center portion 40, the adhesive should not be placed so as to cause adhesion of the absorbent material to the detachment flap 46.

As further shown in FIG. 3B, the absorbent material 70 is impregnated with a band of moisture barrier material 76 so as to form a moisture barrier. The band of moisture barrier material 76 is preferably created prior to the application of the absorbent material 70 to the central portion 40. The moisture barrier material can for example comprise wax, as disclosed in U.S. Pat. No. 4,983,416 (the contents of which are hereby incorporated by reference). The moisture barrier material can be printed on, i.e. directly transferred from an applicator surface to the absorbent material 70, or alternatively can be sprayed or otherwise applied with a pump onto the absorbent material 70. In a preferred embodiment, the moisture barrier material is a water-insoluble polymer such as Fast Drying Polyurethane (available from the Minwax Company). If polyurethane is used, it can be used either straight from the container or diluted with certain organic solvents, e.g., isopropyl alcohol, reagent alcohol (ethanol), heptane, and/or ethyl acetate. Other polymer materials that can be used include polyacrylates and polyvinyl alcohols. Other materials which can be used to form a moisture barrier include those used in the paper industry as sizing materials used for controlling the porosity of paper, such as starch.

FIGS. 3A and 3B illustrate an advantageous method of manufacturing a sample tab 50 according to the present invention. The method comprises providing a piece of rigid backing material comprising a substantially planar surface, in this case the blank 12, and then attaching a piece of absorbent material 70 impregnated with the band of moisture barrier material 76 to the substantially planar surface of the rigid backing material. The portion of the absorbent material 70 comprising the sample collection member 90 is preferably cut or formed from the absorbent material 70 prior to being adhered to the blank 12. Sample collection member 90 should be adhered to the sample tab backing 52 such that only a base portion 94 (best shown in FIG. 2) is adhered to the rigid material of the sample tab backing 52 and such that sample collection end 96 is not adhered to the detachment flap 46.

FIG. 2 shows the sample tab 50 after being removed from the sample collection device 10. With reference to FIG. 2, the band of moisture barrier material 76 is interposed between the handle end 54 in a proximal portion of the sample tab 50 and the sample collection end 96 which extends beyond a distal portion of the handle end 54. The band of moisture barrier material 76 acts to limit the flow of any liquid introduced to the absorbent material 70 of the sample collection end 96 from flowing into the absorbent material base portion 94. This allows a larger piece of absorbent material 70 to be used in forming the sample collection end 96, for ease of manufacturing, but still provides for a more limited and defined area of the sample collection end 96 for retaining an analyte of interest. Although the band 76 is shown in FIG. 3B as a strip whose outer edges parallel each other, the exact configuration of this band 76 is not important (i.e., it could be shaped as a wave), as long as it serves to limit the flow of any liquid introduced to the absorbent material 70 of the sample collection end 96 into absorbent material 70 outside the sample collection end 96 when the sample tab 50 is tested for an analyte.

As described in further detail below, the sample collection end 96 both absorbs analyte from a sample and transfers such analyte to the test device 100 when a test of such sample is performed according to the present invention. The sample tab 50 can thus also be referred to as a sample carrying member in its capacity of retaining a sample and presenting it for analysis by an appropriate test device. By limiting the absorbance of liquid in the sample collection end 96 to an area of predetermined size, the quantity of analyte absorbed from a sample can be better controlled, resulting in improved assay accuracy and consistency. The use of a different absorbent material 70 may affect the amount of an analyte of interest that such a sample collection end 96 can retain, so the appropriate size of the sample collection end 96 may correspondingly change in different embodiments. The transfer of analyte to the test device 100 can be accomplished more efficiently with this configuration, since a fluid applied to the sample collection end 96 for the purpose of reconstituting the analyte contained in the sample collection end 96 of the sample tab 50 will be confined to the sample collection end 96 and will not substantially flow toward the base portion 94, which could carry analyte toward such base portion 94 and away from the test device 100.

As described above, the sample tab backing 52 remains connected to the sample collection device 10 until separated from it through the application of pressure or other force to the sample tab backing 52 by a user. The sample tab 50 can be removably secured to the collection device 10 in other ways as well. For example, in alternative embodiments (not shown) the sample tab 50 can be removably secured by an adhesive applied to a portion of the sample tab backing 52 which overlaps with the collection device 10, for example the exterior side 32 of the base member 30 (shown in FIG. 3E), or by a separate piece of material having an adhesive backing which secures the sample tab backing 52 to the remainder of the sample collection device 10. Thus while the sample tab 50 is secured to the sample collection device 10 during the process of collecting a sample, the sample tab 50 is designed to be removed from the collection device 10 and used with the test device 100 as described in further detail below.

In a preferred embodiment of the present invention, a portion of the sample tab 50, such as the handle end 54, comprises a shape which is not bilaterally symmetrical. Handle end 54 can comprise any or all of the structure of sample tab 50 other than the absorbent material 70. In this embodiment, the receptacle 130 of the test device 100 is sized and shaped so that the sample tab 50 can be received in only a pre-selected orientation. Sample tab 50 thus cooperates with the receptacle 130 in a unique way, such as in a lock-and-key manner. This feature of the present invention ensures that the sample collection end 96 of the sample tab 50 is appropriately directed and is placed in communication with sample pad 120 and ultimately with chromatographic material 160 when it is present in the receptacle 130.

When a sample liquid or a liquid used in an assay of the present invention (such as a liquid carrying an analyte of interest and/or a detection reagent) is able to pass from one element of the present invention to a second element, whether directly or via an intervening element, the two elements are described as being in communication with each other. Communication generally involves physical contact between the elements (including intervening elements), but physical contact is not required as long as such a liquid is able to travel from one element to the other. Elements of the invention are said herein to be in communication (or in liquid communication) even in the absence of a liquid, as long as such elements cooperate in such a way that when the sample or assay liquid is present it is able to flow from one element to the other.

In the embodiment shown in FIG. 2, handle end 54 of the sample tab 50 comprises corner elements 56 and 57 which occur on a different horizontal plane with respect to vertical line A-A which runs from the sample collection end 96 through the handle end 54 and thus impart a bilaterally asymmetrical configuration to the handle end 54 of the sample tab 50. The sample tab 50 of FIG. 2 is likewise bilaterally asymmetrical along an axis perpendicular to line A-A. Bilateral asymmetry of the sample tab 50 as used herein can refer to asymmetry along one or more than one axis.

The assembly of a sample collection device 10 according to the present invention is shown in FIGS. 3A-3E. Once the absorbent material 70 and filter material 80 are secured to the central portion 40 and window portion 20, respectively, and after the interior side 26 of the window portion 20 is folded toward the interior side 48 of the central portion 40 along fold line 28, as shown in FIG. 3B, the interior side 26 of the window portion 20 is secured to the interior side 48 of the central portion 40 to form base member 30 of the sample collection device 10. The base member 30 comprises a body having opposed interior surfaces, namely interior side 34 (as seen in FIG. 3C) and exterior side 32 (seen in FIG. 3E) of the base member 30. An adhesive such as that used to adhere the absorbent material 70 and/or the filter material 80 can be used to form the base member 30. As shown in FIG. 3C, the sample collection end 96 of the sample tab 50 is in communication with the base member window 22 when the base member 30 has been formed, and while the sample tab 50 remains removably secured to the base member 30. In this way, when a sample is applied to the window 22, sample liquid flows through the filter material 80 in the window 22 and then into the absorbent material 70 of the sample collection end 96 of sample tab 50.

A cover member 60 is preferably included with the sample collection device 10 (though such a cover is not necessary for the successful operation of the sample collection device 10). As shown in FIG. 3C, the cover member 60 can be moved into a closed position with respect to the base member 30 by folding the interior side 64 of the cover member 60 toward the interior side 34 of the base member 30 along fold line 66. The cover member 60 can be joined to the base member 30 by a hinge, such as the crease at the fold line 66, or alternatively the cover member 60 can be a separate piece (not shown) attached for example by adhesive. The hinge can be an integral part of the sample collection device 10, as in the illustrated embodiments, or can also be a separate component. The hinge is preferably made of the same material as the sample collection device 10, but can be a different material compatible with the base member 30 and the cover member 60.

The cover member 60 is adapted to cover at least the window 22 when in a closed position with respect to the base member 30, and the interior side 64 of the cover member 60 is also preferably in physical contact with the interior side of the base member. The cover member 60 thus helps to protect someone handling the collection device 10 from coming into contact with a sample placed on the collection device 10 and also protects the sample from contamination and potentially from degradation due to exposure to light or to other elements that might otherwise be able to contact the sample.

The cover member 60 is reversibly secured to the base member 30. In the embodiment illustrated in FIGS. 3C and 3D, cover member 60 is reversibly secured to the base member 30 by means of a tab 62 on the cover member 60 which cooperates with tab lock 25. In such an embodiment it is advantageous that the cover member be rigid, but it must be capable of flexing in order to be able to position the tab 62 in the tab lock 25. The cover member 60 can also be reversibly secured to the base member 30 by other means, such as those described below for closing the test device 100.

The assembled sample collection device 10, as shown in FIG. 3D, is preferably substantially planar, as are the cover member 60 and base member 30 components. While other configurations are possible, a planar configuration facilitates delivery of the collection device via mail or courier to a facility which then tests the sample. While the embodiment shown in FIGS. 1-3E is constructed from a single sheet of material which is folded to create two panels, the sample collection device 10 can alternatively be constructed from multiple pieces or layers of material that are laminated or otherwise attached together.

As shown in FIG. 3E, detachment flap 46 serves to cover the area behind the window 22, i.e. on the exterior side 32 of the base member 30. When a liquid-containing sample is applied through the window 22 of the base member 30, the detachment flap 46 (in cooperation with the sample tab backing 52, while it is attached to the base member 30) substantially prevents sample liquid from coming into contact with the exterior side 32 of the base member 30, or with a user who might be in contact with the exterior side 32.

One feature of the sample collection device 10 which serves to protect the sample collection end 96 of the sample tab 50 is the design of the detachment flap 46. The detachment flap 46, comprising a distal flap edge 44 secured at a distal end to the base member 30 of the sample collection device 10, further comprises a proximal edge 45 removably secured at a proximal end of the detachment flap 46 to the sample collection device 10 and/or to the distal end of the sample tab handle 54. The sample tab 50 comprises the sample collection end 96, which as shown in FIG. 2 comprises a piece of absorbent material 70 extending distally beyond the distal end of the handle 54. While the sample tab 50 and the proximal edge 45 of the detachment flap 46 are removably secured to the sample collection device 10, the distal end of the sample tab handle 54 and the proximal edge 45 of the detachment flap 46 are in physical contact or close proximity, and the proximal edge 45 of the detachment flap 46 covers at least a portion of the absorbent material 70 of the sample collection end 96.

In this embodiment the exterior side 32 of the base member 30 of the sample collection device 10 comprises a rigid material having a substantially planar surface. The detachment flap 46 and sample tab handle 54 are formed from the material of the substantially planar surface, i.e. they comprise an integral part of the same piece of material. The proximal edge 45 of the detachment flap 46 is adapted to detach from the base member 30 and/or from the distal end of the sample tab handle 54, for example by causing any material bridges along proximal edge 45 joining the detachment flap 46 to the sample tab 50 to become separated. The perforations in detachment flap sides 43 are preferably complete cuts through the exterior side 32 of the base member 30, but if they comprise incomplete or partial perforations of the exterior side 32 they should be adapted to separate the detachment flap sides 43 from the remainder of the base member 30.

The separation of the proximal edge 45 and preferably the sides 43 of the detachment flap 46 creates a flap of material (i.e. the detachment flap 46). The proximal edge 45 of the detachment flap 46 is adapted to extend away from the substantially planar surface to provide clearance for the absorbent material 70 of the sample collection end 96 when the sample tab 50 is removed from the sample collection device 10. Handle end 54 of the sample tab 50 is adapted to extend away from the base member 30 when base member 30 is flexed convexly (i.e. when the center of the exterior side 32 of the base member 30 rises above the plane formed by the shorter edges of the base member), allowing a user to grip the handle end and pull the sample tab backing 52 from the exterior side 32 of the base member 30. When the portion of sample tab 50 abutting the proximal edge 45 is detached from and/or moves away from the proximal edge 45, the detachment flap 46 tends to extend away from the substantially planar exterior surface 32 of the base member 30, which creates a clearance distance between the sample collection end 96 of the sample tab 50, which lies under the detachment flap 46, and the proximal edge 45 of the detachment flap 46. This clearance allows the sample collection end 96 to be removed from the sample collection device 10 without substantially impacting the structural integrity of the absorbent material 70 of the sample collection end 96. Without providing such clearance between the sample collection end 96 and the proximal edge 45 of the detachment flap 46, there is a risk that the sample collection end 96 could be torn or sheared off as it is removed from the sample collection device 10.

In embodiments where the sample to be collected has an unpleasant odor, the cover member 60 can further include an odor masking agent. For example, the cover member 60 can include a deodorant or perfume, and/or an odor absorbing agent such as baking soda or charcoal.

Once a sample is collected by the sample collection device 10, it can be tested for an analyte of interest in a test device 100 of the present invention. The test device 100 comprises a base member 110 (also referred to as a test device body) and a cover member 150 having opposed surfaces 151 and 152. The test device 100 can be made from the same types of materials as the sample collection device 10, and is preferably made from laminated SBS.

The interior side 112 of the base member 110 includes a receptacle 130 adapted to receive the sample tab 50 of the collection device 10, preferably the handle portion 54 of the sample tab 50. The receptacle 130 can comprise for example a depression or cavity in the test device base member 110. In embodiments in which the test device 100 is molded from a plastic or other material, the receptacle 130 is simply molded to the desired shape to fit or otherwise cooperate with a sample tab 50. Alternatively, the base member 110 can be constructed from two pieces of material attached together, in which case the base 131 of the receptacle 130 comprises the lower layer 114 of the base member 110 of the test device 100, while the sides of the receptacle are the inner surface of a portion of the upper layer 115 from which a form has been cut. In the embodiment shown in FIGS. 4 and 5A the two pieces of material are hingedly connected and formed from a single blank, in this case a four panel blank of which two panels cooperate to form the base member 110 and two other panels form the cover member 150. In an alternative embodiment, the receptacle 130 can comprise an opening in the test device base member 110, i.e. without a lower layer. Such an embodiment would however advantageously include clips or other supports to maintain the sample tab 50 in the receptacle when placed therein. The sample tab 50 can also be optionally maintained in the receptacle 130 by means of an adhesive substance in the receptacle 130.

The base member 110 of the test device 100 further includes a sample pad 120 for receiving analytes from the sample collection end 96 of the sample tab 50. The sample pad 120 is preferably constructed from several layers of material. The uppermost layer of the sample pad 120, which is in direct or at least in fluid contact (i.e., in communication) with the sample collection end 96 of the sample tab 50 when sample tab 50 is positioned in the receptacle 130, comprises an absorbent sample pad material which is inert, i.e. it does not bind (or does not significantly bind) or react with the analyte of interest. The absorbent sample pad material can be made of any absorbent material that will hold liquid sufficiently so that liquid from a sample (typically a reconstituted sample), including buffers or other assay reagents can be accumulated in the absorbent sample pad material and drawn through the chromatographic medium 160 when it is placed in communication with the chromatographic material 160. Typical materials for the absorbent sample pad material include, but are not limited to, glass fiber, porous plastic, cellulose, filter paper, and combinations of glass fiber and cellulose. The size and shape of the sample pad 120 can be chosen according to the volume of fluid used in the assay.

Below the sample pad material is preferably a layer of foam or cushioning material (not shown). The cushioning material should be an elastic material which resists compression and tends to spring back to its original conformation. When the cover member 150 is closed over the test device 100 of the present invention and the conjugate pad 124 contacts the sample collection end 96 of the sample tab 50, the conjugate pad 124 preferably slightly compresses the cushioning material of the sample pad 120, which causes the cushioning material to exert pressure back on the sample collection end 96. This serves to maintain the sample collection end 96 in communication with the conjugate pad 124.

If the rigid material comprising the test device 100 which lies directly below this layer of cushioning material is sufficiently non-absorbent and resistant to water and/or other reagent fluids used to detect the analyte of interest, then no other layers are necessary, and the cushioning layer can be secured to the test device 100, such as with an adhesive. If the material of the cushioning layer is easily damaged, a stronger piece of material 122, such as LEXAN™ polycarbonate (available from GE Structured Products, Pittsfield, Mass.), can be bonded to the underside of the cushioning material to give structural strength to the combination and allow it to be attached to the test device 100 during manufacturing without undergoing damage.

The test device 100 further includes a piece of chromatographic material 160 used to detect the presence of an analyte of interest in a sample. In a preferred embodiment, the chromatographic material is attached to the cover member 150. In this embodiment, a conjugate pad 124 is attached to the cover member 150 and is in communication with the sample pad 120 and or the sample collection end 96 of the sample tab 50 by means of a conjugate ribbon (not shown). The conjugate ribbon, which can be made from a non-woven material such as polyester, is in communication with and preferably overlays the conjugate pad 124 in order to smooth the transfer of assay buffer and reconstituted sample into the conjugate pad 124. The conjugate pad 124 can generally be constructed in the same way as sample pad 120, except that it contains assay reagents, as described below. In a preferred embodiment, the conjugate ribbon, conjugate pad 124 and chromatographic material 160 are attached to another piece of material, such as LEXAN™ polycarbonate prior to being attached as a unit to the test device 100.

When the interior side 151 of the cover member 150 is moved toward the interior side 112 of base member 110 by bending cover member 150 along fold line 102, and when the test device 100 is thereby closed, conjugate pad 124 is placed in communication with the sample pad 120, thereby allowing any liquid in the sample pad 120 on the base member 110 (which may contain an analyte of interest) to flow into the conjugate pad 124 on the cover member 150 and then into the chromatographic material 160.

The chromatographic material 160 in this embodiment is preferably in the opening or window 170, such that the assay results obtained from performing a test with the chromatographic material 160 can be visualized through the window 170 in the cover member 150. In this embodiment the piece of the chromatographic material 160 is attached to the cover member 150, generally to the interior surface 151 of the cover member 150 and/or to the window 170, and preferably extends across the window 170. At least a portion of the chromatographic material 160 is visible from the window 170, i.e. it is within or beneath the window 170, and this portion should include an immobilized capture reagent which binds an analyte of interest being assayed. In this way the results of a test performed with the chromatographic material 160 can be visualized by a user while the cover 150 of the test device 100 is closed. The window 170 can include a sheet of transparent material such as LEXAN™ polycarbonate interposed between the chromatographic material 160 and the exterior side 152 of the cover member 150, if the chromatographic material 160 isn't already attached to a transparent material such as polycarbonate. While the use of a window 170 is preferred in the present invention, assay results can also be viewed by opening the cover member 150 and visualizing the chromatographic material 160 after an appropriate amount of time has elapsed to allow the assay to be completed (e.g., 5 minutes), thus making the window 170 an optional feature of the present invention.

Figure 4:
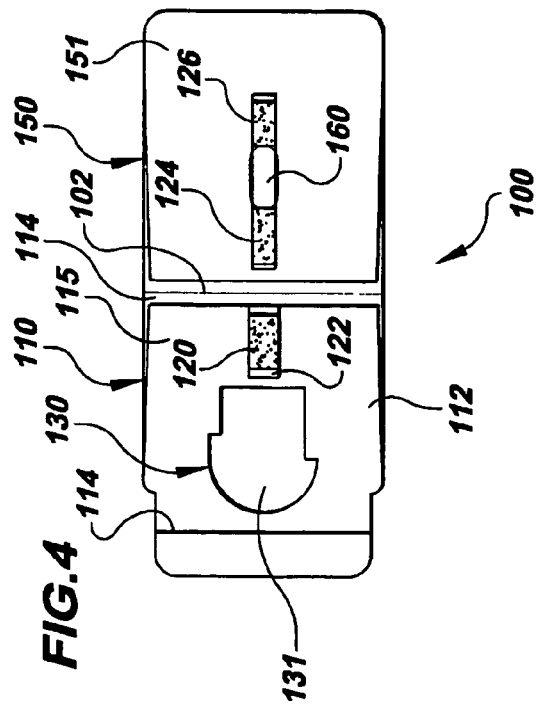
FIG. 4 is a top plan view of the interior side of a test device according to the present invention.

In the embodiment shown in FIGS. 4 and 5A, the chromatographic material 160 is attached to the interior surface 151 of the cover member 150 and is placed across the window 170. The cover member 150 and receptacle 130 cooperate so as to place the chromatographic material 160 in communication with a sample being assayed when the sample tab 50 is contained in the receptacle 130 in a pre-selected orientation and when the cover member 150 is attached to the body 110 of the test device. In this embodiment the chromatographic material 160 is in communication with an absorbent pad 126 at a second end of the chromatographic material 160. The absorbent pad 126 absorbs liquid that flows across the chromatographic material 160 and ensures that analytes of interest are wicked across the chromatographic material 160. The system of the present invention is particularly useful for immunochromatographic assays. The chromatographic material can be any suitable material which can serve as a substrate that can provide an indication of the presence of an analyte of interest, in particular a visible indication. For example, a test strip that can be a liquid-conductive solid phase material to which a detection reagent can be immobilized can be used. It can be a material such as nitrocellulose, to which an appropriately charged detection reagent, such as a monoclonal antibody, can be immobilized. A preferred liquid-conductive solid phase material is a nitrocellulose membrane having a pore size of at least about 1 micron.

Nitrocellulose membranes best adapted for use in connection with immunochromatography of this type have a pore size of about 5-20 microns. The selection of particular pore size dictates the flow rate of the assay. Depending upon the particular application, a faster or slower flow rate may be indicated and an appropriate solid phase material selected. Alternatives to nitrocellulose such as filter paper or a nylon membrane can also be used.

To facilitate handling, it is desirable to provide a backing to the nitrocellulose membrane. A thin plastic sheet stock (e.g., polycarbonate or polystyrene) can be cut to provide a suitable water resistant backing for the chromatographic material 160. Such sheet stock is selected so as not to interfere with the reading of a test result. For example, the selection of a white or clear sheet stock is generally preferred. In an alternative embodiment, the liquid conductive solid phase material can be sandwiched between such water resistant sheet stock, for example so that information or other indications can be made on the sheet stock.

Samples which can be tested with the system of the present invention include biological fluids such as blood, urine, semen, saliva, or excrement, preferably from a human subject, for the detection and/or diagnosis of disease. Samples from animals, plants, food and water can also be tested. The system of the present invention is particularly useful for the detection of FOB.

The sample collection end 96, when in contact with the sample pad 120, is adapted to communicate with the chromatographic material 160 and the conjugate pad 124. The conjugate pad 124 should be in communication with the sample collection end 96 of the sample tab 50 and with the chromatographic material 160; and should be located in a liquid path (i.e. in communication) between these two elements. The conjugate pad provides a matrix for the deposition of a labelled detection reagent which is free to migrate when reconstituted. As used herein, the term "reconstituted" shall be used to indicate the placing of a sample, analyte or assay component into a liquid, whether by suspending, solubilizing, rehydrating, or other means, so that the sample, analyte or assay component can be carried by the liquid through components of the test device 100. Whether a sample and/or an analyte is suspended, dissolved, or otherwise carried in such a liquid will depend on the sample, analyte, and liquid involved. Samples to be analyzed can be applied in liquid or dried form. However, if the analyte of interest is not stable in an aqueous or other liquid environment, it is preferred that the sample be dried in order to preserve such analyte. When testing for the analyte in a desiccated sample, the sample contained in the sample collection end 96 is solubilized, such as through rehydration, and the labelled detection reagent within the conjugate pad 124 is also reconstituted. If analyte is present in the sample, the labelled reagent binds to the analyte and the complex is carried to a detection zone of the chromatographic material 160.

To perform a sandwich immunoassay, the labelled detection reagent is typically a labeled specific binding partner to the analyte, such as a monoclonal or polyclonal antibody specific for a first epitope of the analyte of interest, coupled to a detectable label. A specific binding partner is a member of a pair of molecules that interact by means of specific non-covalent interactions that depend on the three-dimensional structures of the molecules involved. Typical pairs of specific binding partners include antigen-antibody, hapten-antibody, hormone-receptor, nucleic acid (e.g., DNA or RNA) strand-complementary nucleic acid strand, substrate-enzyme, inhibitor-enzyme, carbohydrate-lectin, biotin-avidin, and virus-cellular receptor. Antibodies can include both intact antibody molecules of the appropriate specificity and antibody fragments as well as chemically modified intact antibody molecules and antibody fragments.

The detectable label can be coupled to an antibody or other specific binding partner by any of the applicable techniques known in the art including, for example, covalent bonding and passive adsorption. The detectable label is typically mobile, in that it can migrate through the chromatographic medium 160 with the antibody or other specific binding partner, whether free or bound to an analyte.

The detectable label may be a direct or an indirect label. A direct label is a label which is readily visible in its natural state, either to the naked eye, or with the aid of optical devices. A label which is visible only in the presence of external stimulation, such as ultraviolet light, is also considered to be a direct label. Examples of direct labels include dye sols (e.g., colloidal carbon), metallic sols (e.g., colloidal gold, silver, or iron), fluorescent particles and colored latex particles. A preferred metallic label is colloidal gold, while a preferred non-metallic colloidal label is colloidal carbon. Colloidal carbon labels for labeling of specific binding partners are described, for example, in U.S. Pat. No. 5,529,901 to Van Doorn et al., while colloidal gold labels are described in U.S. Pat. No. 6,528,323, both incorporated by this reference. Antibodies labeled with colloidal gold are commercially available, for example from Sigma Chemical Company, St. Louis, Mo.

Indirect labels require the addition of one or more developing reagents, such as substrates, to facilitate detection. Such labels include enzymes such as alkaline phosphatase and horseradish peroxidase.

In order to conduct an immunoassay with the chromatographic material 160, an immobilized capture reagent should also be included in the chromatographic material 160. The immobilized capture reagent is also typically a monoclonal or polyclonal antibody which is specific for a second epitope or range of epitopes on the analyte of interest. Alternatively, when one of the specific binding partners is labeled with biotin, the secondary specific binding partner (i.e., the immunochromatographic capture reagent) can comprise a molecule conjugated to avidin. Thus, analyte present in the sample, whether bound by the detection reagent or not, is bound by the immobilized binding reagent in the detection zone of the chromatographic material 160. If a direct label is employed, a visible line appears on the chromatographic material 160 as bound label accumulates in the detection zone. The appearance of this line may be diagnostic for the presence of analyte of interest in the sample.

A control zone can also be integrated into the chromatographic material, 160. The function of a control zone is to convey a signal to the user which indicates only that the testing process is complete and that the binding interaction which results in the detectable signal (unrelated to detecting the analyte of interest) has taken place as expected. For example, if the detection reagent is a murine monoclonal antibody linked to a detectable label, then the control zone can comprise an "anti-mouse" polyclonal antibody immobilized to the liquid-conductive solid phase material, preferably downstream of the detection zone. At least some of the detection reagent not bound in the detection zone through a sandwich interaction involving the analyte of interest should ultimately bind in the control zone.

The test device cover member 150, test device base member 110, and sample tab 50 are adapted to cooperate so that the sample collection end 96 of the sample tab 50 is in liquid communication with the chromatographic material 160 when the handle portion 54 of the sample tab 50 is contained in the receptacle 130 of the test device base member 110 and when the test device cover member 150 is reversibly attached to the test device base member 110. In this embodiment the results of an assay performed with the test device 100 are visible through the window 170 when the cover member 150 is closed, and the bound portion of the detection reagent is present on the portion of the piece of chromatographic material 160 that is in the window 170. In an alternative embodiment, in which the chromatographic material 160 is attached to the base member 110, the portion of the chromatographic material 160 showing the assay results can be viewed without the cover member 150 being placed over or attached to the base member 110, or a window can be provided in the cover member 150 to allow viewing of the assay results through such window when the cover member 150 is attached to the base member 110.

Figure 5B:
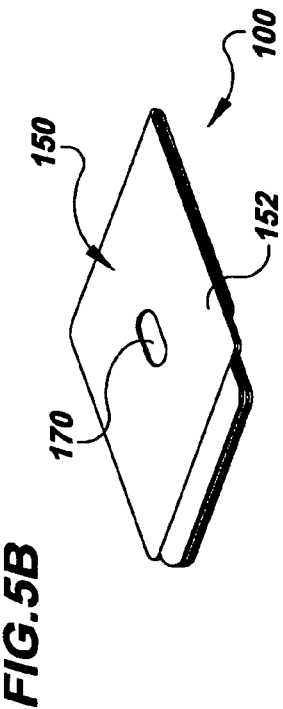
FIG. 5B is a perspective view of a test device of the invention in a closed position.

The test device 100 is preferably reversibly secured in a closed position with a closure capable of maintaining sample collection end 96 in communication with the sample pad 120 and conjugate pad 124 when the test device 100 is closed. A variety of closures can be used, such as for example a strip of adhesive on the interior side 151 of the cover member 150 and/or on the interior side 112 of the base member 110. In another embodiment, such a closure, appropriate for use when the rigid material of the test device 100 is SBS, can comprise a bevel as shown in FIGS. 5A and 5B. The bevel closure of the testing device according to the present invention can be the bevel closure disclosed in U.S. Pat. No. 5,441,698 of Norell, incorporated herein by this reference. To form a bevel closure, a bevel edge 114 is created on the base member 110. Typically, the bevel angle is between about 5 degrees and about 30 degrees from the vertical, and more preferably the angle is from about 8 degrees to about 10 degrees from the vertical. The cover edge 154 is undercut, and the bevel angle and the undercut angle are approximately equal.

To close the test device 100 using such a bevel closure, the cover member 150 is rotated about fold line 102 (a hinge) such that the cover member 150 and base member 110 are brought together with a protruding corner of the cover edge 154 brought against the upper surface of the bevel edge 114. The cover member 150 and base member 110 are urged together, slightly flexing the test device 100, allowing the protruding corner of the cover edge 154 to be displaced beneath an overhanging of the bevel edge 114 on the base member 110. With the entire length of the cover edge 154 thus captured by the overhanging corner of the bevel edge 114 (shown in FIG. 5B), the test device 100 is closed.

In a further embodiment of the present invention (not shown), the chromatographic material 160 is located on the base member 110, i.e. on substantially the same planar surface as the receptacle 130 and the sample pad 120, and is in liquid communication with the sample pad 120. As with other embodiments, this test device 100 comprises a receptacle 130 that is adapted to cooperate with a sample tab 50 of the sample collection device 10 of the present invention which is not bilaterally symmetrical, so that the sample collection end 96 of the sample tab 50 is placed in communication with the chromatographic material 160 when the sample tab 50 (and in particular the handle end 54 of the sample tab 50) is received in the receptacle 130. If a cover member 150 is used with this embodiment, the cover member preferably reversibly securable to the base member 110 and includes a window 170 through which the results of the test performed on the chromatographic material can be visualized.

In another embodiment of the present invention, the system of the present invention comprises a sample collection device 10 and test device 100 as described above, except that the sample tab 50 and the receptacle 130 with which it cooperates to perform an assay according to the invention do not have an asymmetrical configuration. In this embodiment, the sample tab 50 is removably secured to the base member 30 of the sample collection device 10 as described previously. The cover member 150 of the test device 100 in this embodiment preferably includes a window 170 which provides communication between the interior side 151 and the exterior side 152 of the cover member 150. A portion of the piece of chromatographic material 160 attached to the cover member 150 (preferably to the interior side 151 of the cover member 150) is in the window and the assay results are visible in the portion of the piece of chromatographic material 160 within the window 170 by a user of the test device. In this embodiment the test device cover member 150, test device base member 110, and sample tab 50 are still adapted to cooperate so that the sample collection end 96 of the sample tab 50 is in communication with the chromatographic material 160 when the handle portion 54 of the sample tab 50 is contained in the receptacle 130 of the test device base member 110 and when the test device cover member 150 is removably secured to the test device base member 110.

Both the sample collection device 10 and the test device 100 according to the present invention are preferably single-use devices, meant to be disposed of and not reused after the collection of a sample with the sample collection device 10 and/or after the performance of an assay with the test device 100. In an alternative embodiment, portions of the test device 100 can be used more than once. As will be clear to one of skill in the art, the sample collection pad 120, absorbent ribbon, absorbent pad 126, conjugate pad 124 and the chromatographic material 160 of the test device 100 should not be reused, so in an embodiment of the invention in which part of the test device 100 is reused the sample collection pad 120, absorbent ribbon, absorbent pad 126, conjugate pad 124, and chromatographic material 160 should be removably or reversibly secured to the test device 100. Following the performance of an assay, the used sample collection pad 120, absorbent ribbon, absorbent pad 126, conjugate pad 124, and chromatographic material 160 are removed and replaced with an unused sample collection pad 120, absorbent ribbon, absorbent pad 126, conjugate pad 124, and chromatographic material with which a subsequent assay can be performed.

EXAMPLE 1

Construction of a Sample Collection Device

A sample collection device 10 as shown in FIGS. 1-3E is constructed as follows. A blank 12 approximately 9¼ inches long and 2¼ inches wide made of SBS is die-cut as shown in FIG. 1. The blank 12 includes a cover member portion 60, a center portion 40 and a window portion 20. The center portion 40 includes a sample tab perforation 42 around the entire periphery of sample tab backing 52. Sample tab perforation 42 is not a complete perforation, such that sample tab backing 52 remains connected to the remainder of the blank 12. Such perforations cooperate with collection distal flap edge 44 as well as with a portion of the sample tab perforation 42 to form the detachment flap 46.

The window portion 20 includes an opening or window 22 cut from the blank 12. The window portion 20 further includes a tab lock perforation 24 used to form tab lock 25 (shown in FIG. 3D).

FIG. 3A shows the spatial placement of an absorbent material 70 along placement lines 72 and filter material 80 along placement lines 82. A band of moisture barrier material 76 is applied to the absorbent material 70, and the absorbent material 70 is also pre-cut to form sample collection member 90, both prior to the absorbent material 70 being adhered to the filter material 80. The combined sheet of absorbent material 70 adhered to the filter material 80 is itself then adhered to the window portion 20 with drops of adhesive placed approximately ¼ inch from the edges of the combined sheet (including on the base portion 94 of the sample collection member 90). The combined sheet is placed on the window portion 20 of the blank 12 so as to cover the window 22.

The interior side 26 of the window portion 20 is then folded along line 28 until it is brought into contact with and adhered to the interior side of center portion 40 to form the base member 30. The placement of the combined sheet of absorbent material 70 and filter material 80 on the center portion 40 is such that the detachment flap 46 and at least a portion of sample tab backing 52 is covered.

The cover of the device is next formed by folding cover member portion 60 along line 66 such that the interior surface 64 of the cover member 60 is brought toward the interior surface 34 of base member 30. The tab lock 25 cooperates with a tab 62 on the cover member 60 to maintain the sample collection device 10 in a closed position.

EXAMPLE 2

Construction of a Test Device

Figure 5:
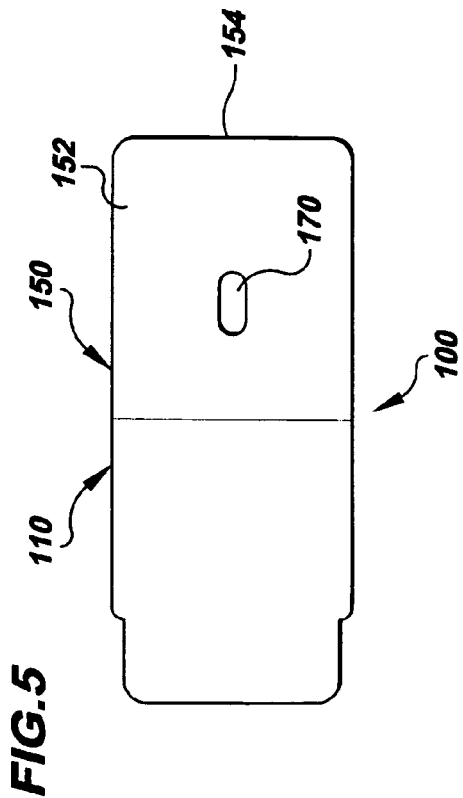
FIG. 5 is a bottom plan view of the exterior side of a test device according to the present invention.

A sample test device as shown in FIGS. 4-5B is constructed as follows. The test device 100 comprises a base member 110 (approximately 3 inches long and 2½ inches wide) and a cover member 150 (approximately 2½ inches long and 2½ inches wide) connected by a hinge (fold line 102). The interior side 112 of the base member 110 includes a receptacle 130 adapted to receive the handle end 54 of the sample tab 50 of the collection device 10. In the embodiment shown in FIGS. 4 and 5A the base member 110 is constructed from two pieces of material attached (folded) together, and the base 131 of the receptacle 130 comprises the lower layer 114 of the base member 110 of the test device 100. The sides of the receptacle are the inner surface of a portion of the upper layer 115 from which a form has been cut.

A sample pad 120 for receiving analytes from the sample collection end 96 of the sample tab 50 is attached to the base member 110 of the test device 100. Receptacle 130 is adapted to receive the sample tab 50 (shown in FIG. 5A) in only one way, thereby assuring that the sample collection end 96 of the sample tab 50 is placed in contact with sample pad 120. The handle end 54 of the sample tab 50 and corresponding receptacle are formed with a shape which is not bilaterally symmetrical to accomplish this. Below the sample pad is a layer of foam or cushioning material attached to a strip of LEXAN™ polycarbonate.

A piece of LEXAN™ polycarbonate to which has been attached a conjugate ribbon in contact with a conjugate pad 124, and which is in further contact with a strip of chromatographic material 160 is also attached to the cover member 150. The chromatographic material 160 is positioned in an opening or window 170 in the cover member 150 so that results obtained from performing a test with the chromatographic material 160 can be visualized through the window 170. The piece of LEXAN™ polycarbonate is interposed between the chromatographic material 160 and the exterior side 152 of the cover member 150.

The conjugate pad 124 and chromatographic material 160 are further positioned on the cover member 150 such that when the cover member 150 is closed over the base member 110 by means of the hinge, the conjugate pad 124 contacts the sample collection end 96 and the sample pad 120, and the conjugate pad 124 slightly depresses the cushioning material of the sample pad 120. A absorbent pad 126 is placed in contact with a second end of the chromatographic material 160. The absorbent pad 126 absorbs liquid that flows across the chromatographic material 160 during an assay.

To close the test device 100, the cover member 150 is rotated about fold line 102 such that the interior side 151 of the cover member 150 and the interior side 112 of the base member 110 are brought together with a protruding corner of the cover edge 154 brought against the upper surface of the bevel edge 114. The cover member 150 and base member 110 are urged together, slightly flexing the test device 100, allowing the protruding corner of the cover edge 154 to be displaced beneath an overhanging of the bevel edge 114 on the base member 110. With the entire length of the cover edge 154 thus captured by the overhanging corner of the bevel edge 114 (shown in FIG. 5B), the test device 100 is closed.

The sample collection device and test device of the present invention have been described above in embodiments in which only one sample is tested for the presence of an analyte. However, in other embodiments a single device can collect or analyze more than one sample. If the sample collection device is being used to collect fecal samples, multiple samples can be collected over a predetermined period of time. For example, three different samples can be collected over, e.g., the course of three days with the embodiments described below. Collecting and then analyzing a plurality of samples makes it more likely that an analyte of interest, such as blood in the stool, if present, will be detected, as blood may not be present in a patient's stool in every sample, or the portion of the stool in which blood can be found is not sampled for detection. When performing assays with a test device according to this aspect of the invention, individual samples can be tested one or more at a time, but multiple samples are preferably assayed at the same time with this embodiment.

In describing this alternative embodiment of the present invention, like figure numbers (e.g., 12 and 212) will denote similar device elements. Elements with the same name (though a different assigned figure number) will also generally be made in the same way and with the same materials unless otherwise noted.

EXAMPLE 3

Construction of a Sample Collection Device for Collecting Multiple Samples

A sample collection device as shown in FIGS. 6-8 is constructed as follows. A blank 212 approximately 9⅛ inches long and 3⅞ inches wide made of SBS is die-cut as shown in FIG. 6. The blank 212 includes a cover member portion 260, a center portion 240 and a window portion 220. The center portion 240 includes a sample tab perforation 242 around the entire periphery of sample tab backing 252. Sample tab perforation 242 is not a complete perforation, such that sample tab backing 252 remains connected to the remainder of the blank 212. Such perforations cooperate with collection distal flap edge 244 and detachment flap sides 243 as well as with a portion of the sample tab perforation 242 to form the detachment flap 246.

The window portion 220 includes an opening or window 222 cut from the blank 212. The window portion 220 further includes a tab lock perforation 224 used to form tab lock 225 (shown in FIG. 7).

A band of moisture barrier material 276 (seen in FIG. 9A) is applied to the absorbent material 270, and the absorbent material 270 is also pre-cut to form sample collection member 290, both prior to the absorbent material 270 being adhered to the filter material (not shown). The combined sheet of absorbent material 270 adhered to the filter material is itself then adhered to the window portion 220 with drops of adhesive placed approximately ¼ inch from the edges of the combined sheet (including on the base portion 294 of the sample collection member 290). The combined sheet is placed on the window portion 220 of the blank 212 so as to cover the window 222.

The interior side 226 of the window portion 220 is then folded along line 228 until it is brought into contact with and adhered to (with the glue beads) the interior side of center portion 24Q to form the base member 230. The placement of the combined sheet of absorbent material 270 and filter material on the center portion 240 is such that the detachment flap 246 and at least a portion of sample tab backing 252 is covered.

The cover of the device is next formed by folding cover member portion 260 along line 266 such that the interior surface 264 of the cover member 260 is brought toward the interior surface 234 of base member 230. Each of the tab locks 225 cooperate with a corresponding tab 262 on the cover member 260 to maintain the sample collection device 200 in a closed position.

EXAMPLE 4

Construction of a Test Device for Collecting Multiple Samples

Figure 9B:
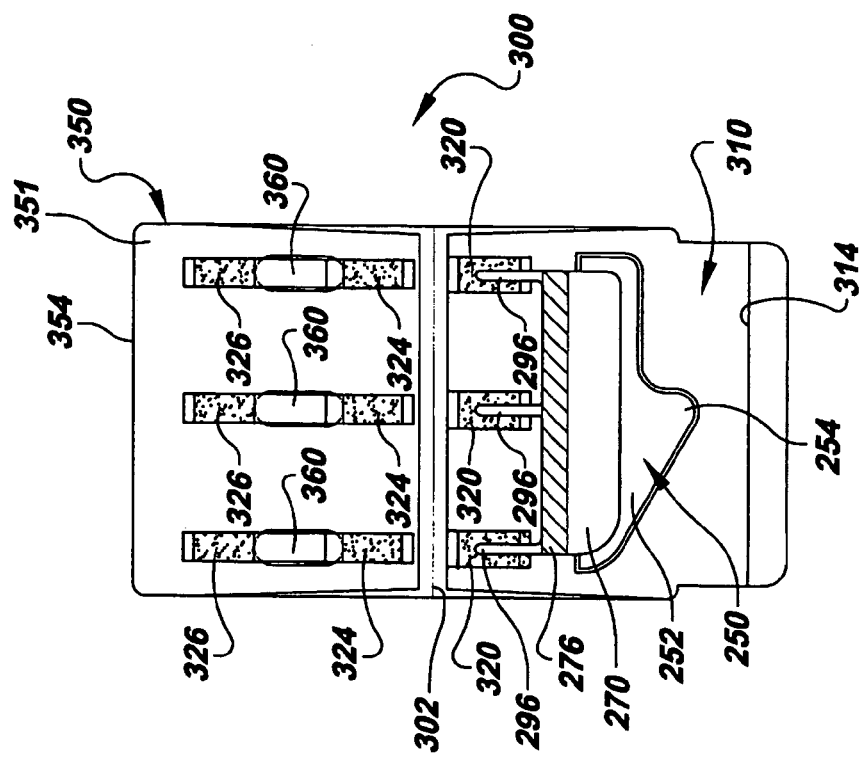
FIG. 9B is a top plan view of the test device of FIG. 9 with the sample collection tab (shown in FIG. 9A) placed in the test device.
Figure 9A:
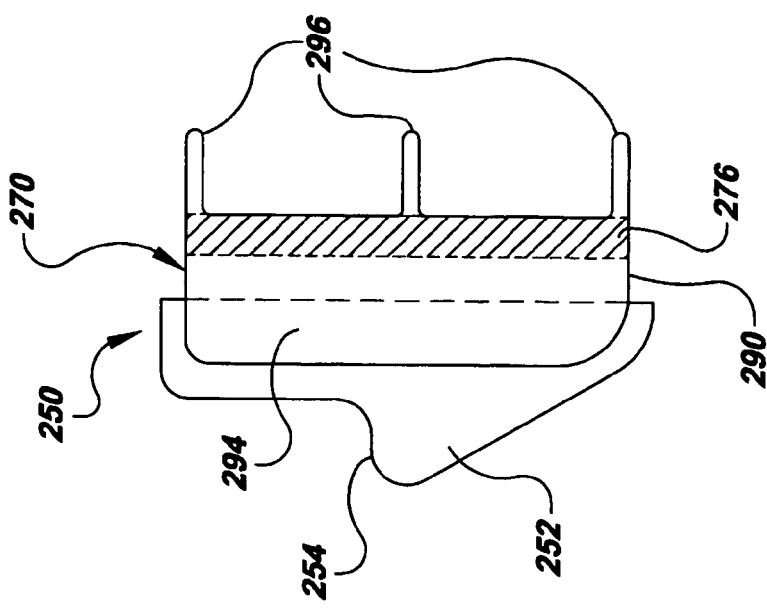
FIG. 9A is a top plan view of a sample collection tab for use with the test device of FIG. 9.

A test device for testing three samples as shown in FIGS. 9-11 is constructed as follows. The test device 300 comprises a base member 310 (approximately 3 inches long and 3¼ inches wide) and a cover member 350 (approximately 2⅞ inches long and 3¼ inches wide) connected by a hinge (fold line 302). The interior side 312 of the base member 310 includes a receptacle 330 adapted to receive the handle end 254 of the sample tab 250 of the collection device 200. In the embodiment shown in FIGS. 9 and 9B the base member 310 is constructed from two pieces of material attached together, and the base 331 of the receptacle 330 comprises the lower layer 314 of the base member 310 of the test device 300. The sides of the receptacle are the inner surface of a portion of the upper layer 315 from which a form has been cut.

Sample pads 320 for receiving analytes from the sample collection ends 296 of the sample tab 250 are attached to the base member 310 of the test device 300. Receptacle 330 is adapted to receive the sample tab 250 (shown in FIG. 9B) in only one way, thereby assuring that the sample collection ends 296 of the sample tab 250 are each placed in contact with one of the sample pads 320. The handle end 254 of the sample tab 250 and corresponding receptacle 330 are formed with a shape which is not bilaterally symmetrical to accomplish this. Below each sample pad 320 is a layer of foam or cushioning material.

On the cover member 350 are placed conjugate pads 324 in contact with strips of chromatographic material 360 also attached to the cover member 350. The strips of chromatographic material 360 are positioned in windows 370 in the cover member 350 so that results obtained from performing tests with the strips of chromatographic material 360 can be visualized through the windows 370. Sheets of a clear polymer material such as LEXAN™ polycarbonate are interposed between the chromatographic material 360 and the exterior side 352 of the cover member 350.

The conjugate pads 324 and strips of chromatographic material 360 are further positioned on the cover member 350 such that when the cover member 350 is closed over the base member 310 by means of the hinge, the conjugate pads 324 contact the sample collection ends 296 and the sample pads 320, and the conjugate pads 324 slightly depress the cushioning material of each of the sample pads 320. Further sample pads 326 are placed in contact with a second end of each of the strips of chromatographic material 360. The further sample pads 326 absorb liquid that flows across the strips of chromatographic material 360 during an assay.

To close the test device 300, the cover member 350 is rotated about fold line 302 such that the interior side 351 of the cover member 350 and the interior side 312 of the base member 310 are brought together with a protruding corner of the cover edge 354 brought against the upper surface of the bevel edge 314. The cover member 350 and base member 310 are urged together, slightly flexing the test device 300, allowing the protruding corner of the cover edge 354 to be displaced beneath an overhanging of the bevel edge 314 on the base member 310. With the entire length of the cover edge 354 thus captured by the overhanging corner of the bevel edge 314 (shown in FIGS. 10 and 11), the test device 300 is closed.

In the embodiment of the test device 300 described in Example 4, the test device 300 can alternatively comprise a molded, hard "clamshell" which contains the test device elements. A multiple-assay configuration of the present invention will in most cases be wider than a single assay embodiment, and such a wider configuration may cause contact between a sample collection end 296 of the sample tab 250 and a sample pad 320 to be greater for the assays run on the outer edges of the device as compared with assay(s) performed on the interior strips of chromatographic material 360 if the material of test device 300 is not sufficiently rigid (as may be the case if SBS is used). This can result in a faster chromatographic flow rate on the outer chromatographic strips and cause inaccurate test results. As an alternative to a hard plastic clamshell, a less rigid material like SBS can be used together with strips of more rigid material (not shown) in the base member 310 and cover member 350 to provide additional support. In embodiments using a hard clamshell, the clamshell may be reusable, though certain elements of the test device 300 (described above) should not be reused.

EXAMPLE 5

Collecting a Fecal Specimen for Testing

A fecal sample may be collected in ways known to the art. A sample is preferably obtained which is free of interfering substances, and which is not contaminated by matter from another individual. In one method, a patient from whom a sample is to be collected makes use of a toilet to collect a sample. The toilet (free of toilet bowl cleaners and other chemicals) is first flushed. The lid and seat of the toilet are lifted, and a piece of plastic wrap is placed over the toilet bowl. The plastic wrap can be about two feet long and about a foot wide. The plastic wrap should be secured across the rim of the toilet bowl, preferably across the back half, allowing the middle of the plastic wrap to hang down just above the water. A piece of tissue is then preferably placed on top of the plastic wrap. The patient then lowers and sits on the seat and has a bowel movement, thereby placing stool on the tissue. Alternatively, the tissue can be used without the plastic wrap. In this case the tissue is placed in the toilet bowl and allowed to float on the surface of the water. The tissue should cover enough of the surface of the water that the stool is placed on the tissue as a result of a bowel movement by the patient. It is important to keep the stool sample from contacting the water in a toilet bowl to the extent possible, as certain analytes, including blood in stool, may only be present on the surface of a stool sample and such analytes are subject to being washed away from the stool sample should they come into contact with water, which could lead then to a false negative test result.

Once the stool sample is obtained, it is applied to the window 22 in communication with the sample collection end 96 of the sample tab 50. Using a flattened stick or other applicator, a pea-sized sample of stool is collected and placed on the filter paper 80 on one side of the window 22 and spread across half of the window. The applicator is commonly made from wood or can be made from a substantially non-absorbent inert material.

A second pea-sized sample is next preferably collected from a second area of the stool sample, placed on the filter paper 80 on the other side of the window 22, and spread across the remaining half of the window. The stool samples applied to the filter paper 80 are preferably then mixed so that the sample collection end 96 comes into contact with material from both samples from the stool sample. In one embodiment an application area for the first and second samples can be printed on the absorbent material 70 (or alternatively on the filter paper 80) in order to guide the user as to where to apply the samples.

The sample is next allowed to dry. A cover may be placed over the sample tab window, as long as it does not seal the window and prevent drying. The collection device should not be placed in a bag or other container that would prevent drying during this time. In embodiments with multiple collection windows, stool samples may be collected over multiple days in the same manner. The collection device is then sent, such as via mail or courier, to a testing facility.

EXAMPLE 6

Performing an Assay with the Test Device

To perform a test for an analyte of interest in a sample collected as described above, the sample tab backing 52 or at least a portion thereof is separated from the exterior side 32 of the base member 30 of the sample collection device 10, for example by flexing the base member 30 of the device, so that the handle end 54 of the sample tab can be gripped by a user. The sample tab 50 is then carefully removed from the sample collection device, such as by pulling the sample tab 50 up and away from the exterior side 32 of the base member 30. As described above, at least the proximal edge 45 of the detachment flap 46 also separates from the exterior side 32 to provide clearance for the sample collection end 96 of the sample tab as it is removed from the sample collection device 10.

The sample tab or sample carrying member 50, and in particular the handle portion 54 of the sample tab 50 is next placed in the receptacle 130 of the test device 100 as shown in FIG. 5A. Sample tab 50 is bilaterally asymmetrical and is sized and shaped so that the it can be received in the receptacle 130 only in a pre-selected orientation which ensures that the sample collection end 96 is placed in communication with the sample pad 120 of the test device 100.

A test for an analyte of interest is next performed with the test device 100. An appropriate buffer for the analyte to be tested for is next placed on the sample pad 120 and sample collection end 96 of the sample tab 50 in order to reconstitute the analyte, which is typically dry or desiccated. To test for fecal occult blood 3 drops of sample extraction buffer are applied. The sample extraction buffer will be different for different analytes as well as for different antibodies or other detection reagents. For a fecal specimen being assayed for the presence of blood, the extraction buffer preferably comprises an aqueous solution at controlled pH which includes salts, surfactant, and phosphate buffered saline. The antibody preferably binds an epitope on a human globin chain.

The cover member 150 is then placed on the test device, and a chromatographic material comprising a detection reagent is thereby placed in communication with the sample in the sample tab. Reconstituted sample flows from the sample collection end 96 of the sample tab 50 (and from the sample pad, if any sample has migrated into the sample pad after the application of the buffer) into the conjugate pad 124. The cover member 150 is then closed and assay results read through window 170 after 5 minutes.

Although the present invention has been described in considerable detail with reference to certain preferred versions thereof, other versions are possible. For example, the collector and test component need not be rectangular, but can be in other configurations such as an oval, circular, and polygons having more than four sides. Therefore, the spirit and scope of the appended claims should not be limited to the description of the preferred versions contained herein.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. A sample collection device comprising:
   (a) a body having first and second opposed surfaces, wherein the first opposed surface is substantially planar;
   (b) sample tab removably secured to the first opposed surface, comprising a handle having a proximal end and a distal end;
   (c) an absorbent material for receiving a fecal sample, the absorbent material being attached to the distal end of the sample tab; and
   (d) a flap connected to the first opposed surface, the flap comprising a proximal edge covering at least a portion of the absorbent material of the sample tab when the sample tab is removably secured to the first opposed surface;
   wherein the proximal edge of the flap is adapted to extend away from the first opposed surface when the first opposed surface is flexed convexly to provide clearance for the absorbent material when the sample tab is removed from the first opposed surface.

2. The sample collection device of claim 1, wherein the first opposed surface of the body comprises a piece of rigid material, and wherein the sample tab comprises a sample tab backing formed by perforations in the piece of rigid material, the sample tab backing comprising the handle.

3. The sample collection device of claim 1, wherein the flap is formed in the first opposed surface of the body.

4. The sample collection device of claim 1, wherein the absorbent material is impregnated with a band of moisture barrier material separating a sample collection end of the absorbent material from the remainder of the absorbent material.

5. The sample collection device of claim 1, wherein a portion of the absorbent material extends beyond the distal end of the handle.

6. The sample collection device of claim 1, wherein the second opposed surface comprises a window in liquid communication with the absorbent material.

7. The sample collection device of claim 6, wherein the window includes a filter material which allows liquid to flow through the filter material but which inhibits the flow of solids.

8. The sample collection device of claim 6, further including a cover member adapted to cover the window of the second opposed surface.

9. The sample collection device of claim 1, wherein the body of the sample collection device is formed from a cellulose-based material resistant to moisture.

10. A method of collecting a fecal sample, comprising:
(a) providing a sample collection device comprising:
(i) a rigid body having a substantially planar surface;
(ii) a sample tab removably secured to the substantially planar surface of the rigid body, the sample tab comprising a handle having a proximal end and a distal end attached to an absorbent material which carries a fecal sample; and
(iii) a flap having a distal end attached to the substantially planar surface of the rigid body and a proximal end abutting the distal end of the handle;
(b) flexing the rigid body, thereby detaching the proximal end of the handle from the substantially planar surface and causing the proximal end of the flap to extend away from the substantially planar surface; and
(c) pulling the handle away from the flap.

11. A device for the collection and transportation of a fecal sample comprising:
(a) a substantially planar body having front and back opposed surfaces, wherein said front surface includes a sample collection area configured to receive the sample;
(b) a sample collection member removably secured to the back surface of the substantially planar body, wherein a region of the sample collection member is in fluid communication with the sample collection area, wherein said sample collection member is configured to remove a portion of the sample received by the sample collection area when separated from the back surface of the substantially planar body; and
(c) a flap attached to the back surface of the substantially planar body, wherein said flap includes a proximal edge that covers the sample collection area and covers at least a portion of the sample collection member when the sample collection member is removably secured to the back surface.

12. The device of claim 11, wherein the removably secured sample collection member comprises a handle end configured to extend away from the back surface of the substantially planar body when the substantially planar body is flexed, thereby facilitating the detachment of the sample collection member from the back surface of the substantially planar body.

13. The device of claim 11, wherein the flap is configured to extend away from the back surface of the substantially planar body when the sample collection member is detached from the substantially planar body.

14. The device of claim 11, wherein the sample collection member is asymmetrical, wherein the sample collection member is sized and shaped to be received in a pre-selected orientation in a test device.

15. The device of claim 11, further comprising a filter material interposed between the sample collection area and the sample collection member, wherein the filter material allows the flow of liquid and analyte of interest through the filter material to the sample collection member but inhibits the flow of solids.

16. The device of claim 11, further comprising a cover member attached to the front surface, the cover member adapted to cover the sample collection area.

17. The device of claim 11, wherein the sample collection member comprises an area of predetermined size that is in fluid communication with the fecal sample, to remove a substantially consistent quantity of the fecal sample received by the sample collection area when separated from the back surface of the substantially planar body.

* * * * *